(12) United States Patent
Cassidy, Jr.

(10) Patent No.: US 6,450,992 B1
(45) Date of Patent: Sep. 17, 2002

(54) CANNULA INTERFACE

(75) Inventor: Roger R. Cassidy, Jr., Methuen, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 09/346,827

(22) Filed: Jul. 2, 1999

(51) Int. Cl.[7] ............................................. A61M 5/178
(52) U.S. Cl. ................................................ 604/164.01
(58) Field of Search ........................ 604/264, 533–535, 604/538, 539, 523, 164.01, 165.01, 165.02, 165.04, 166.01

(56) References Cited

U.S. PATENT DOCUMENTS

| | | | |
|---|---|---|---|
| 4,896,986 A | | 1/1990 | Terayama |
| 5,171,245 A | * | 12/1992 | Cezena ........................ 606/86 |
| 5,176,662 A | * | 1/1993 | Bartholomew et al. ..... 604/283 |
| 5,391,152 A | | 2/1995 | Patterson .................... 604/165 |
| 5,456,673 A | | 10/1995 | Ziegler et al. |
| 5,743,883 A | * | 4/1998 | Visconti ...................... 604/169 |
| 5,820,614 A | * | 10/1998 | Erskine et al. ............... 604/283 |
| 5,899,888 A | * | 5/1999 | Jepson et al. ................ 604/201 |

FOREIGN PATENT DOCUMENTS

DE      19724282 C1      10/1998

OTHER PUBLICATIONS

Smith & Nephew Endoscopy, Inc., Smith & Nephew Endoscopy 1996 Products Catalog, p. B9, 12/95.

* cited by examiner

*Primary Examiner*—Anhtuan T. Nguyen
*Assistant Examiner*—Ann Lam
(74) *Attorney, Agent, or Firm*—Fish & Richardson P.C.

(57) ABSTRACT

A cannula includes a coupling interface adapted to receive and engage a wide variety of medical instruments having engaging portions which are different. In general, the cannula includes an elongated insertion member having a passage for receiving the medical instrument and a clamping assembly disposed at the proximal end of the elongated insertion member to engage the medical instrument. The clamping assembly includes a second surface axially spaced from the first surface of the elongated insertion member, and a biasing member positioned to bias at least one of the first surface and the second surface axially toward each other and to clamp an engaging portion of the medical instrument between the first and second surfaces.

21 Claims, 10 Drawing Sheets

CANNULA INTERFACE

BACKGROUND OF THE INVENTION

The invention relates generally to a medical instrument cannula.

A cannula is a thin surgical tube inserted into a body cavity or duct through which various medical instruments (e.g. endoscopes, trocars, suture forceps) access the body cavity or duct. Because the same cannula is used to introduce different medical instruments to a particular surgical location (e.g. at different stages of a procedure) damage is minimized to the surrounding tissue. As a result, an increasing number of medical instruments are being developed for use with a cannula.

In certain surgical procedures, it is desirable to fix the medical instrument to the cannula to prevent the instrument from shifting. Many medical instruments, therefore, are designed to releasably interface with a complementary cannula. In one type of interface, the medical instrument includes an engaging portion in the form of a hub having radially extending tabs which are received within a complementary groove or recess formed at the proximal end of the cannula. This arrangement is often referred to as a "Storz-type" interface. However, there is no single, standard releasable interface, even for instruments having a Storz-type interface. Instead, manufacturers of medical instruments have adapted their own, sometimes similar, versions of interfaces for coupling their own medical instruments to a complementary cannula.

However, the dimensions of the hubs of the medical instruments and the geometries of the grooves of the cannulas are sufficiently different to generally prevent using a medical instrument made by one manufacturer with a cannula made by another manufacturer. This can be problematic when a surgeon desires using medical instruments from different manufacturers during the same surgical procedure. In some cases, the coupling designs of the different manufacturers are sufficiently similar that a surgeon may, unsuccessfully, attempt to use non-compatible instruments and cannulas together, which can cause frustration and delay.

SUMMARY OF THE INVENTION

The invention relates to a coupling interface for a cannula adapted to receive and engage a wide variety of medical instruments having engaging portions which are different.

In a general aspect of the invention, the cannula includes an elongated insertion member having a passage for receiving the medical instrument and a clamping assembly disposed at the proximal end of the elongated insertion member to engage the medical instrument. The clamping assembly includes a second surface axially spaced from the first surface of the elongated insertion member, and a biasing member positioned to bias at least one of the first surface and the second surface axially toward each other and to clamp an engaging portion of the medical instrument between the first and second surfaces.

Another aspect of the invention relates the clamping assembly itself and described above. For example, the clamping assembly may be provided as a separate assembly which can be attached to any number of different cannulas.

The clamping assembly advantageously provides a variable space between the first surface and second surface for receiving a wide variety of medical instruments having differently shaped and sized engaging portions. Once the medical instrument is positioned so that its engaging portion is within the space, the biasing member maintains a force on at least one of the first and second surfaces ensuring that the instrument is well secured to the cannula.

Embodiments of the invention may include one or more of the following features.

The clamping assembly of the cannula further includes a user-manipulatable actuator for manipulating the clamping assembly to move at least one of the first and second surfaces toward and away from each other. The first surface and second surface are transverse to the axis of the elongated insertion member with the space between the first surface and second surface defining a channel for receiving the engaging portion of the medical instrument. The actuator includes an opening sized to receive the engaging portion of the medical instrument and is configured to be moved axially away from the elongated insertion section to allow the engaging portion of the medical instrument to be received within the channel. The actuator is then rotated about an axis of the elongated insertion member to engage the engaging portion within the channel in a closed position.

The opening is defined by a pair of opposing straight sides and a pair of opposing rounded sides, the opposing straight sides defining the second surface. The cannula includes an alignment post extending from the first surface of the elongated insertion member to align the engaging portion of the medical instrument to the clamping assembly.

The actuator includes a moveable member and the biasing member is positioned between the movable member and the elongated member. In one embodiment, the biasing member is a spring and is positioned between the moveable member and the first surface, such that axial movement of the actuator toward the second surface compresses the biasing member.

The cannula further includes a cover and a post for mechanically coupling the moveable member to the cover. The cover is removable to facilitate cleaning and replacement of the different parts of the clamping assembly.

The elongated insertion member has a guide slot for receiving the post and guiding the clamping assembly between the opened and the closed positions. The guide slot includes a first section extending axially along the insertion section to a second section which extends circumferentially around the insertion section, the second section extending to a third section extending axially along the insertion section, the post positioned within the first and third sections in the open and closed positions respectively. The passage of the elongated insertion member includes an O-ring seal. A torsion spring may be used to bias the clamping assembly to remain in a rotatably closed position.

In another aspect of the invention, a method of attaching a medical instrument to a cannula is provided. The cannula is of the type having an elongated insertion member having a proximal end with a first surface and a passage extending from the proximal end through a distal end of the insertion member. The method includes the following steps. The medical instrument is introduced through the passage. A clamping assembly is then used to engage an engaging portion of the medical instrument to the proximal end of the elongated insertion member. The clamping assembly includes a second surface axially spaced from the first surface of the elongated insertion member and a biasing member. The biasing member is positioned to bias at least one of the first surface and the second surface axially toward each other and to clamp the engaging portion of medical instrument between the first surface and the second surface.

Embodiments of this aspect of the invention may include one or more of the following features. The clamping assembly further includes the step of manipulating a user-manipulatable actuator to move at least one of the first and second surfaces of the clamping assembly toward and away from each other.

In one embodiment, the first surface and second surface are transverse to the axis of the elongated insertion member and the space between the first surface and second surface define a channel for receiving the engaging portion of the medical instrument. With this arrangement, the method further includes the following additional steps. The actuator is axially moved away from the elongated insertion section to allow the engaging portion of the medical instrument to be received within the channel. The actuator is then rotated about an axis of the elongated insertion member to engage the engaging portion within the channel in a closed position.

Other features and advantages of the invention will become apparent from the following description, drawings and from the claims.

DETAILED DESCRIPTION

Figure 1:
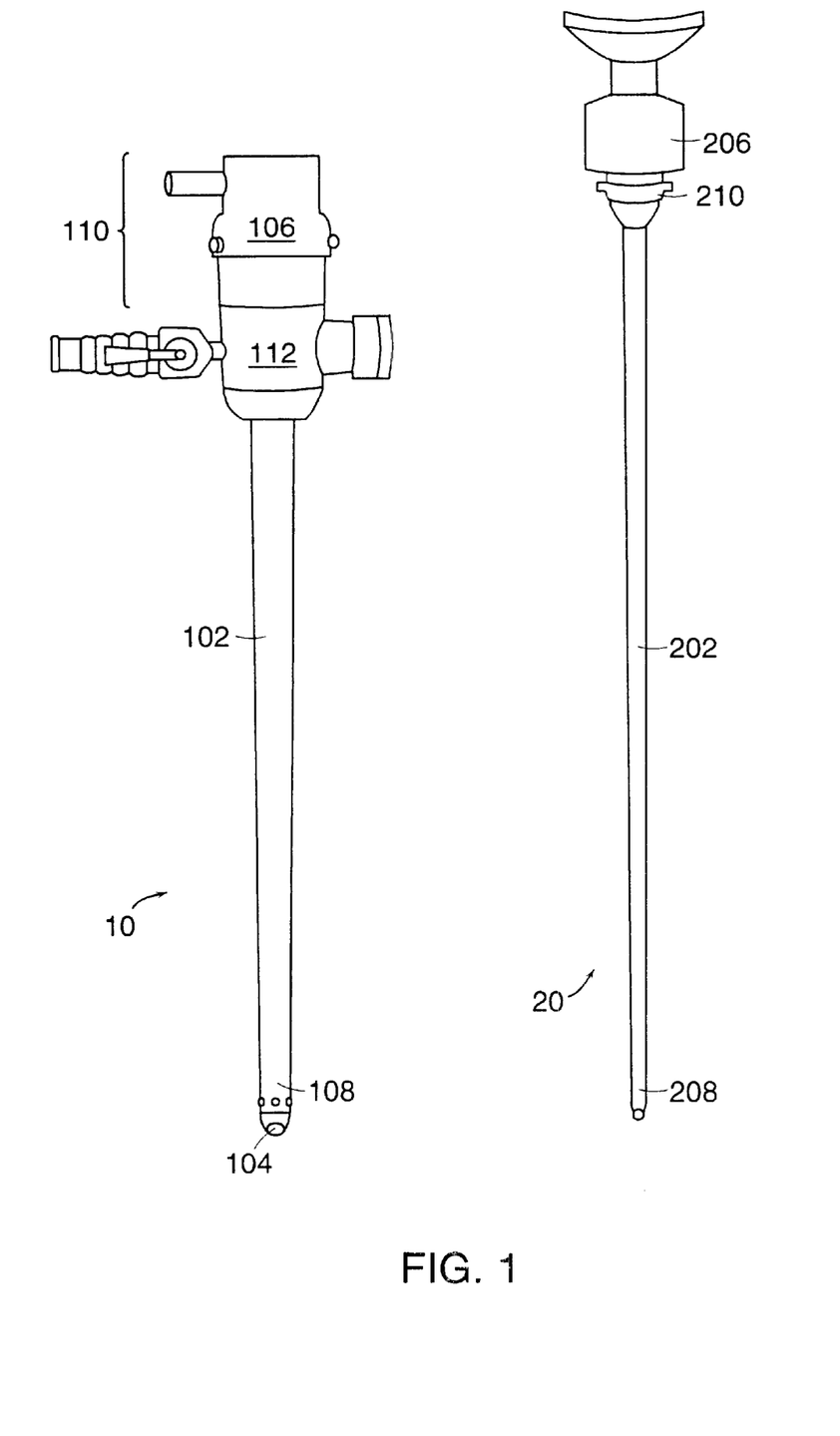
FIG. 1 is a side view of a cannula of the invention and a medical instrument to be received therein.

Referring to FIG. 1, a cannula 10 for receiving a medical instrument 20 (here, an arthroscope) is shown. Cannula 10 has an elongated insertion member 102 with a passage 104 extending from a proximal end 106 to a distal end 108 allowing the medical instrument 20 to extend therethrough. The proximal end 106 of cannula 10 has an inflow set 112 for applying or removing fluid through the passage 104 and a clamping assembly 110 which, as will be described below, allows a wide variety of different medical instruments to be held firmly within cannula 10.

Figure 2A:
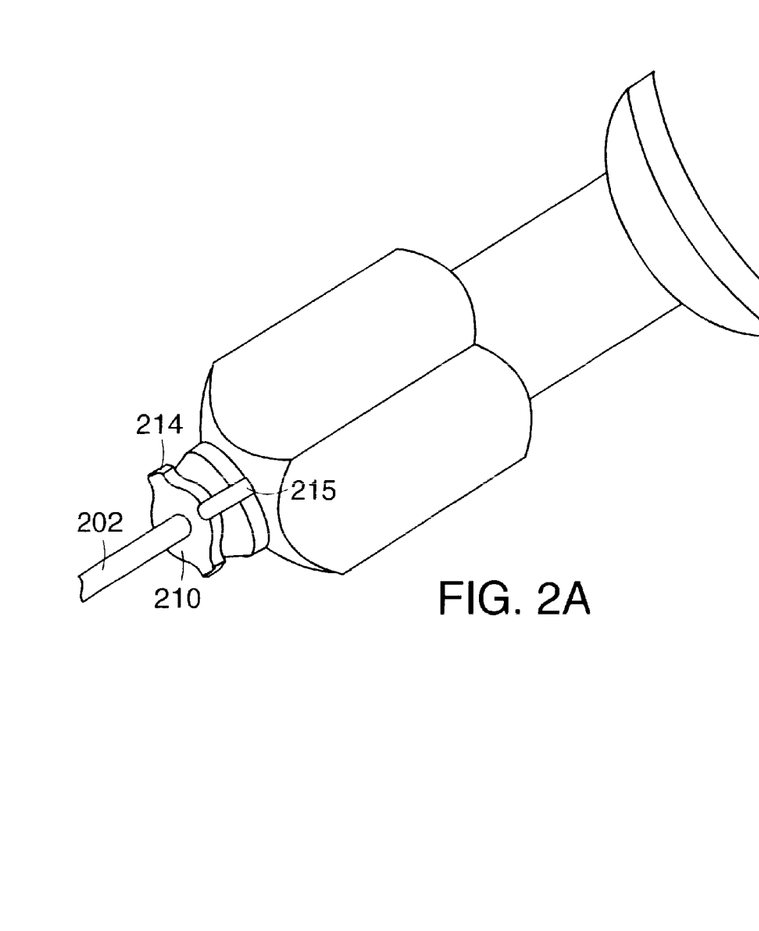
FIG. 2A is a perspective view of a cannula interface of the medical instrument of FIG. 1.
Figure 2B:
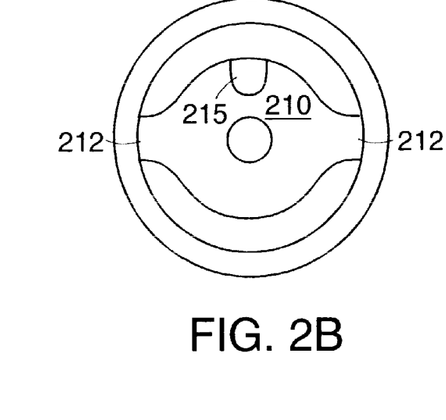
FIG. 2B is an end view of the cannula interface of FIG. 2A.

Referring to FIGS. 2A and 2B, a proximal end 206 of medical instrument 20 includes a Storz-type medical instrument hub 210 having engagement tabs 212 (FIGS. 2A and 2B) which couple to clamping assembly 110 of cannula 10. In general, during a surgical procedure, an elongated insertion member 202 of medical instrument 20 is inserted through passage 104 of cannula 10 until an engaging portion of medical instrument 20, here a medical instrument hub 210 fits within clamping assembly 110. Clamping assembly 110 has a surface which engages an opposing surface of medical instrument hub 210, thereby holding medical instrument 20 firmly within cannula 10.

Figure 2C:
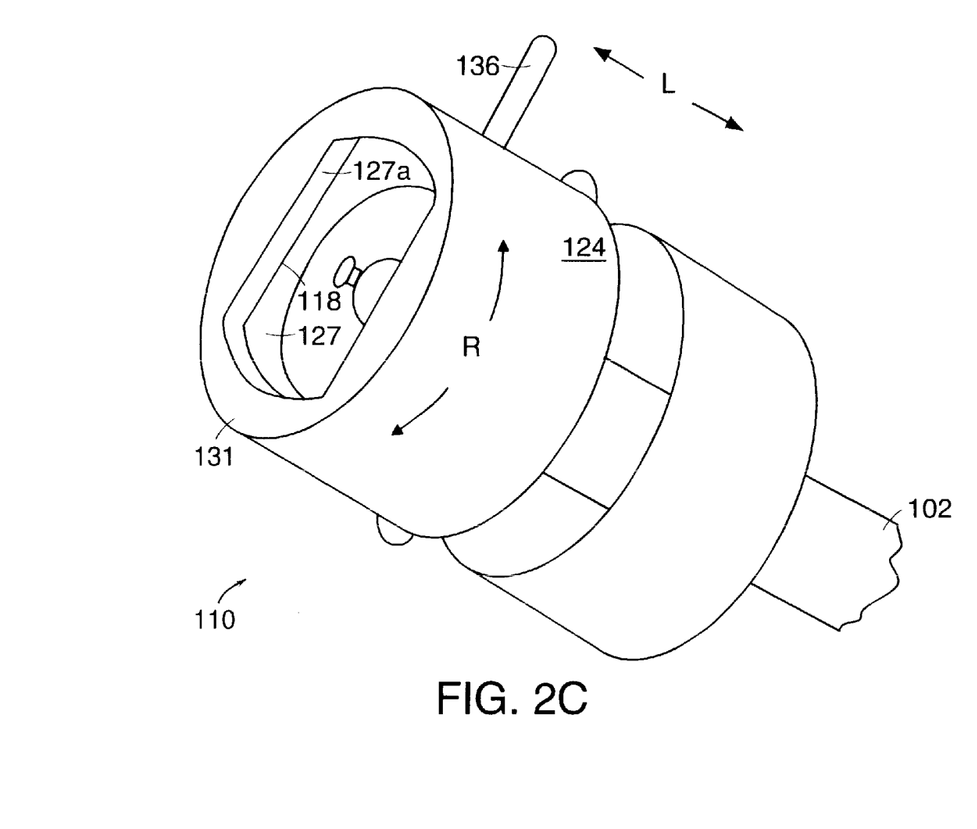
FIG. 2C is a perspective view of the proximal end of the cannula of FIG. 1.
Figure 2D:
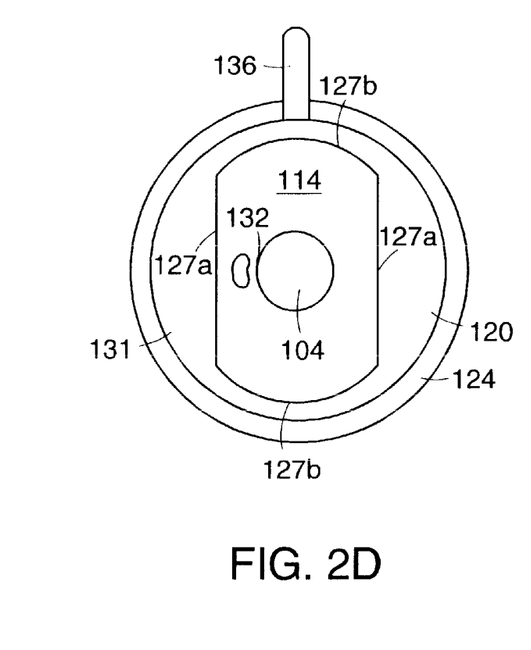
FIG. 2D is an end view of the cannula in FIG. 1.

Referring to FIGS. 2C and 2D, clamping assembly 110 has an open position for receiving medical instrument hub 210 and a closed position for clamping the instrument firmly within the cannula 10. When the clamping assembly is in its open position, instrument 20 is inserted through an opening 114 of passage 104 until the medical instrument hub 210 is within clamping assembly 110. The clamping assembly 110 is then moved to a closed position. In its closed position, the clamping assembly 110 engages the engagement tabs 212 of medical instrument hub 210 to clamp medical instrument 20 to cannula 10.

Figure 3:
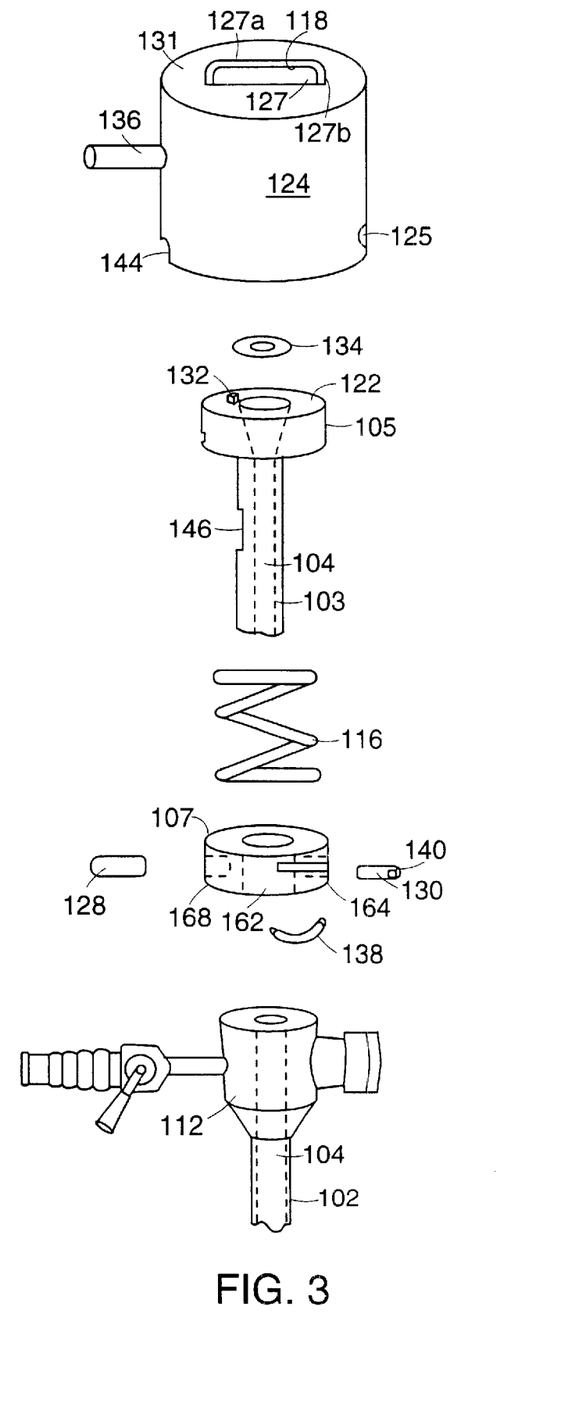
FIG. 3 is an exploded view of the proximal end of the cannula of FIG. 1.

Referring to FIG. 3, cannula 10 includes an extension tube 103, which is press-fit within the proximal end of insertion member 102 and includes a cannula hub 105 having a diameter larger than that of extension tube 103. Cannula hub 105 defines the proximal end of passage 104, shown here in phantom, and includes an O-ring seal 134 which prevents fluid introduced from inflow set 112 from leaking back through the clamping assembly, when the clamping assembly has been moved into its closed position. An alignment tab 132 extends from a first clamping surface 122 of cannula hub 105 and, as will be described below, is received into alignment slot 215 (FIGS. 2A and 2B) of medical instrument hub 210 of medical instrument 20 when the instrument is first received within cannula 10.

Clamping assembly 110 also includes a moveable member 107 and a spring 116, both of which are positioned between the proximal end of insertion member 102 and cannula hub 105. Spring 116 serves as a biasing member for applying an axial force to maintain moveable member 107 against the proximal end of insertion member 102.

Cannula 10 also includes a removable cover 124 positioned over extension tube 103, moveable member 107, and spring 116. Cover 124 includes an end 131 having an underside which defines a second clamping surface 118 opposing first clamping surface 122. Cover 124 also includes an opening 127 with a shape that is complementary to the shape of medical instrument hub 210. In particular, the shape of opening 127 is defined by a pair of opposing rounded sides 127b and a pair of opposing straight sides 127a, which define the edges of the second clamping surface 118. In essence, first clamping surface 122 and second clamping surface 118 define a variably-sized cylindrical recess or channel within which engagement tabs 212 of medical instrument 20 are captured.

A pair of posts 128, 130 are used to mechanically couple cover 124 to diametrically-opposing positions of moveable member 107. This arrangement ensures that cover 124 is properly aligned with moveable member 107. In essence, the combination of cover 124 and mechanically-coupled moveable member 107 provide an actuator for moving clamping assembly 110 between its open, receiving position and closed, clamped position. Cover 124 includes a finger post 136 to assist the user in rotating the cover and moveable member 107 about the axis of cannula 10.

Figure 4:
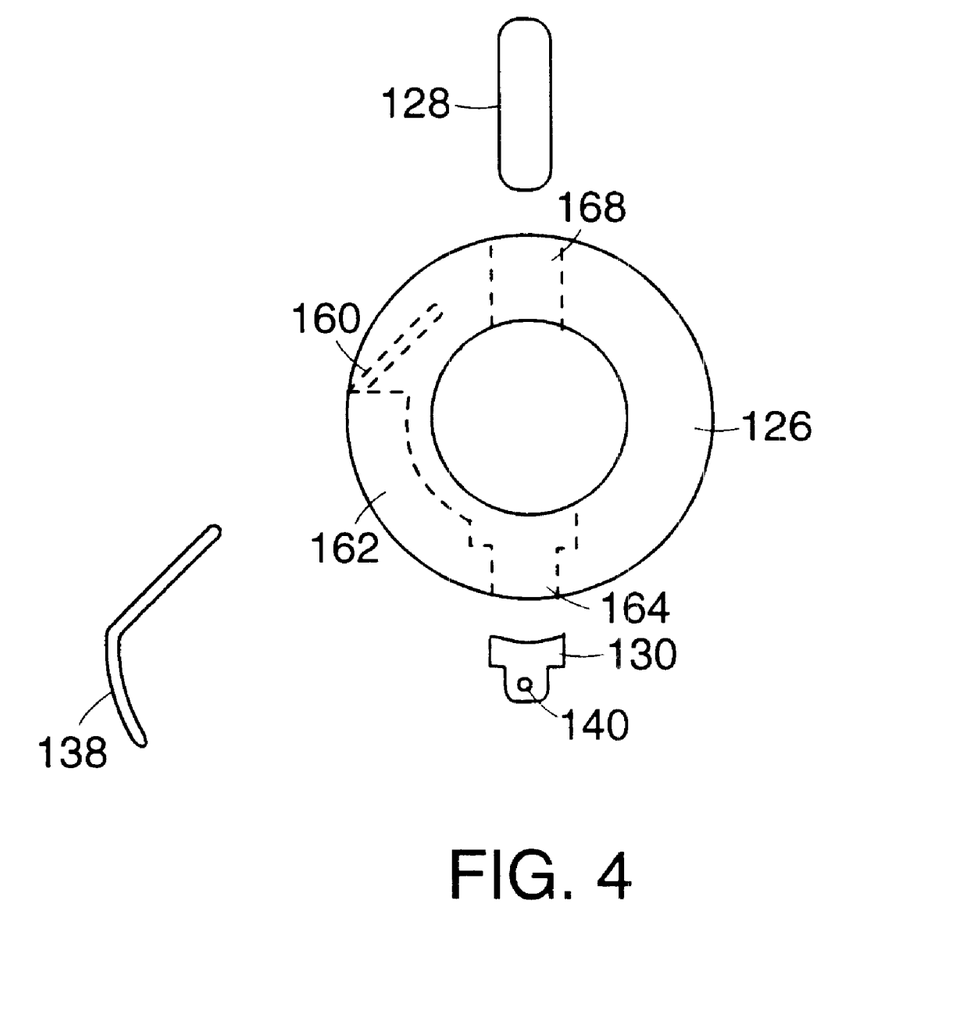
FIG. 4 is an end, exploded view of a moveable member of the cannula of FIG. 1.
Figure 5A:
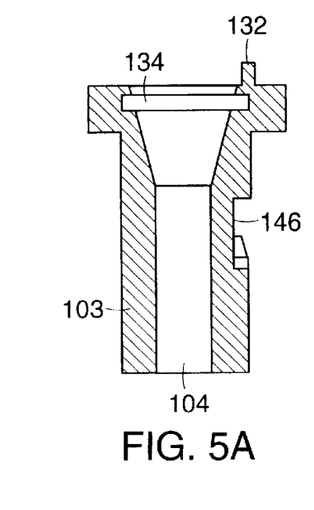
FIG. 5A is a cross-sectional view along the center line of a proximal portion of the elongated insertion section of the cannula of FIG. 1.
Figure 5B:
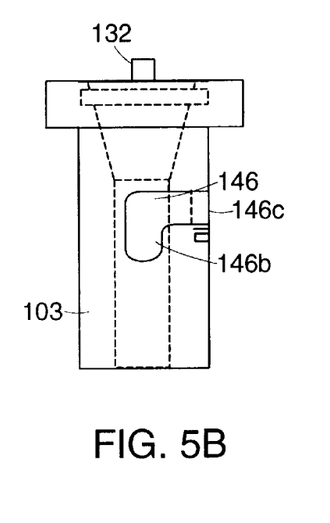
FIGS. 5B and 5C are opposing side views of a proximal portion of the elongated insertion section of the cannula of FIG. 1.
Figure 5C:
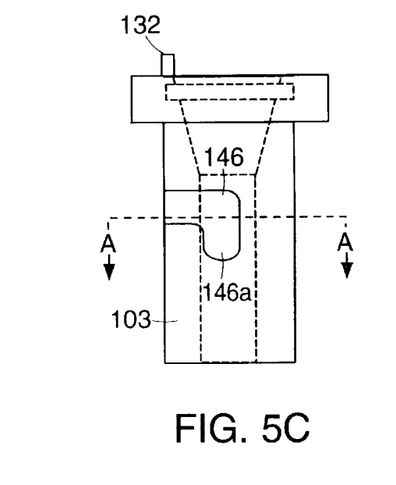
Figure 5D:
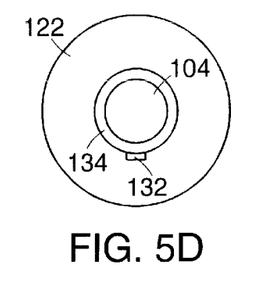
FIG. 5D is an end view of the proximal portion of the elongated insertion section of the cannula of FIG. 1.
Figure 5E:
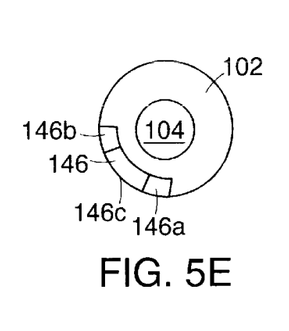
FIG. 5E is a cross-sectional view along line A–A of the proximal portion of the elongated insertion section of FIG. 5C.

Referring to FIG. 4, post 128 is press-fit within hole 168 of moveable member 107. On the other hand, to facilitate removing cover 124 from cannula 10, post 130 is spring-loaded within a hole 164 of moveable member 107. Specifically, moveable member 107 includes a channel 162 within which a wire spring 138 is disposed. Wire spring 138 is fixed at one end within a slot 160 of moveable member 107 and extends circumferentially within channel 162 where its other end is received within a small hole 140 of post 130. To mechanically couple cover 124 to moveable member 107, cover 124 includes an open-ended slot 144 (FIG. 3) which is slid onto post 128 and a hole 125 which receives post 130 when the post is depressed. To remove cover 124 from moveable member 107, post 130 is depressed against the bias of wire spring 13, while cover 124 is slid axially off of moveable member 107. Allowing cover 124 to be removed in this manner advantageously facilitates cleaning and/or replacing of the parts of clamping assembly 110.

In addition to extending through slot 144 of cover 124 and hole 168 of moveable member 126, post 128 also extends within a guide slot 146 of extension tube 103. In general, guide slot 146 of the elongated insertion member 102 directs the movement of moveable member 107 and cover 124.

Referring to FIGS. 5A–5E, guide slot 146 is U-shaped to control the movement of moveable member 107 and cover 124 between the opened and closed positions. Here, guide slot 146 is located on the proximal portion 106 of cannula 10, here extension tube 103. Specifically, guide slot 146 includes a first axial section 146a within which post 128 is positioned when cannula 10 is in its open, receiving position; a second axial section 146b within which post 128 is positioned when the cannula is its closed, clamped position; and a circumferential section 146c between axial sections 146a and 146b.

Operation of clamping assembly 110 of cannula 10 will now be described in conjunction with FIGS. 6A–6C.

Figure 6A:
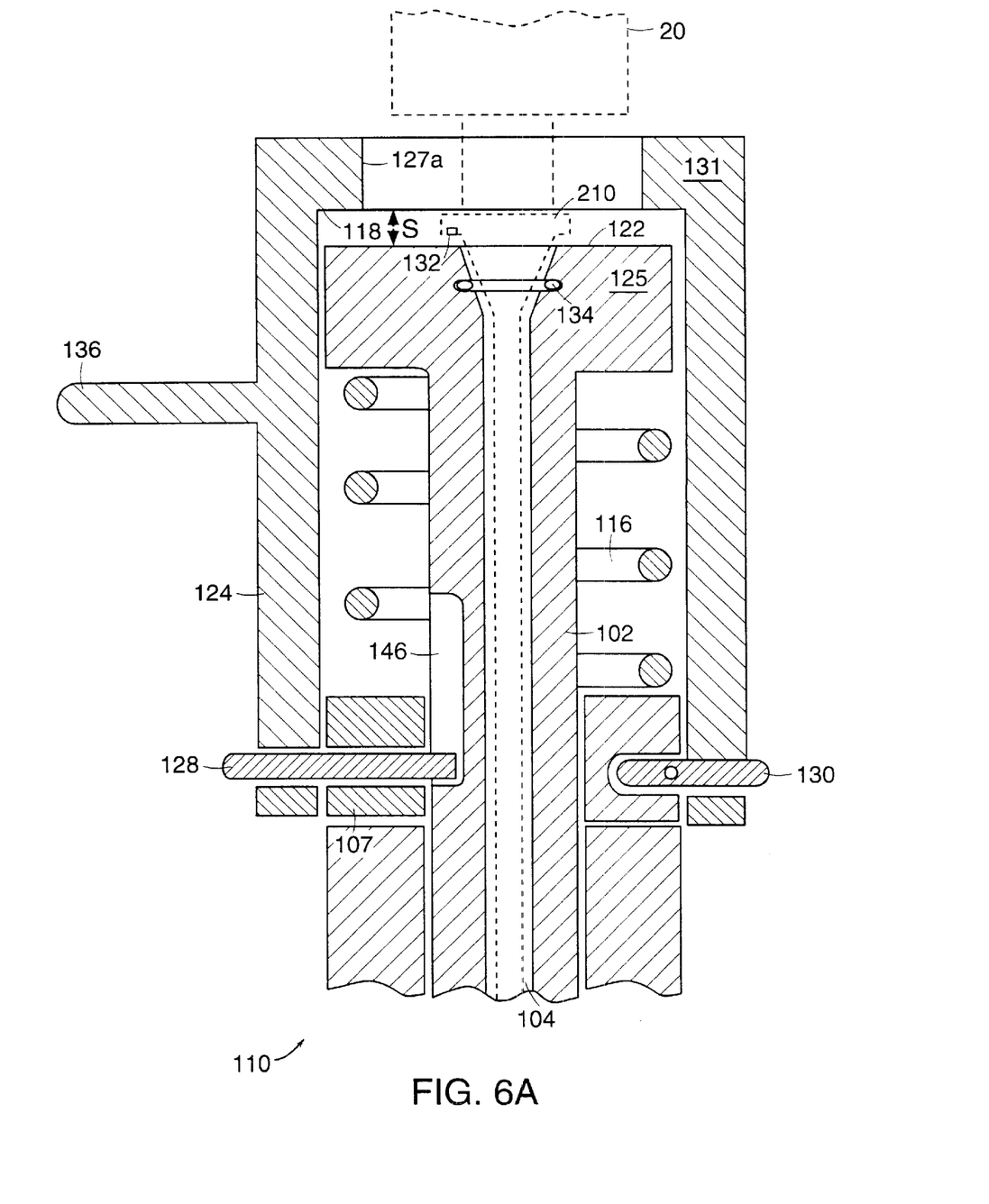
FIG. 6A is a cross-sectional view of the clamping assembly in an open position with a medical instrument shown in phantom.

Referring to FIG. 6A, medical instrument 20 is positioned through passage 104 of cannula 10 with hub 210 aligned with opening 127 of cover 124 until medical instrument hub 210 contacts and is aligned with first clamping surface 122 of hub 105. The medical instrument hub 210 is properly aligned for clamping when the user positions alignment tab 132 of hub 105 within alignment slot 215 of hub 210. Once inserted into clamping assembly 110, a portion of medical instrument hub 210 rests against seal 134 in passage 104. In this position engagement tabs 212 are positioned adjacent opposing rounded sides 127b of opening 127.

Figure 6B:
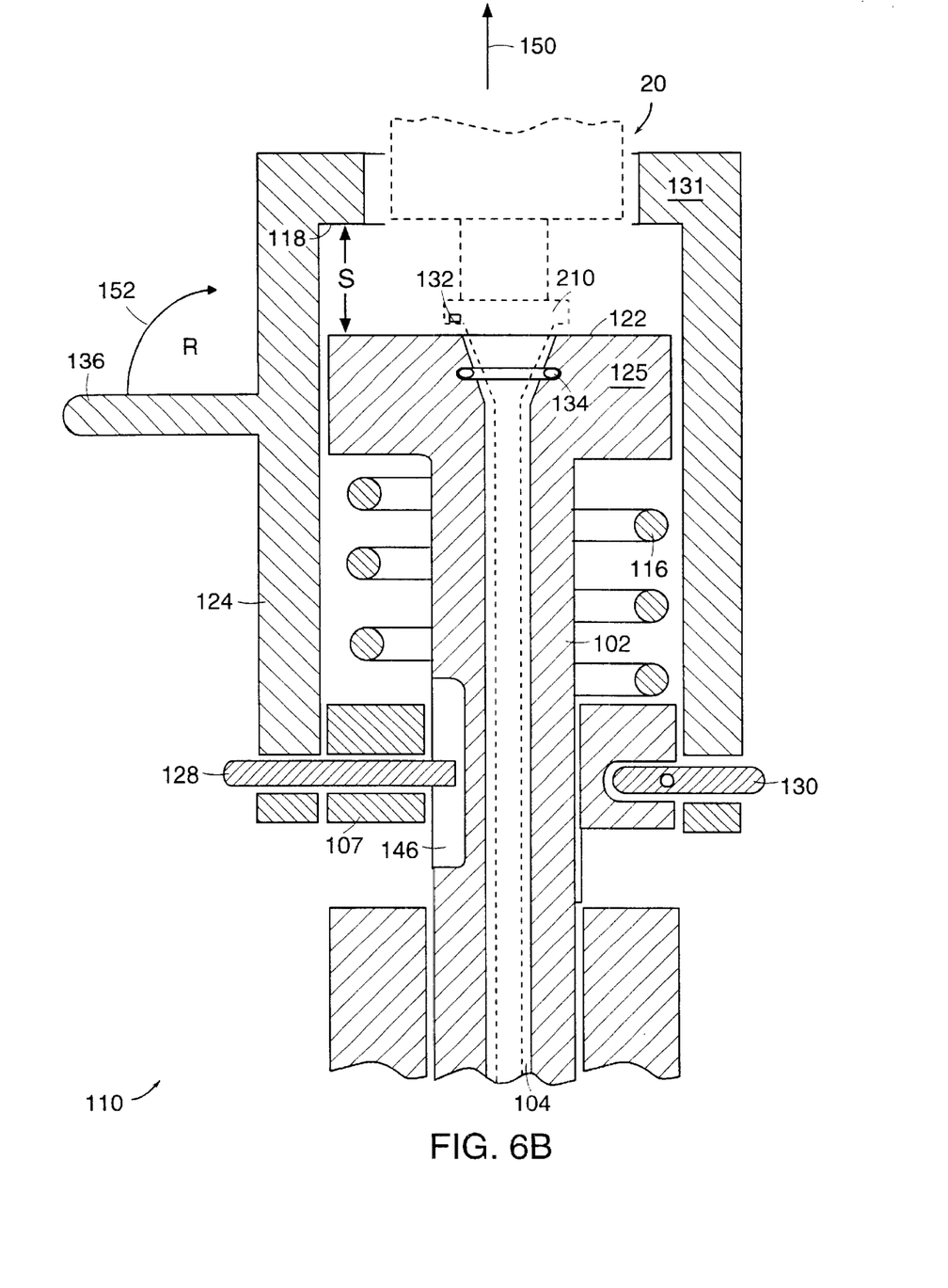
FIG. 6B is a cross-sectional view of the clamping assembly between open and closed positions with a medical instrument shown in phantom.

Referring to FIG. 6B, to secure medical instrument 20 within clamping assembly 110, the user grasps cover 124, for example, with the help of finger post 136, and applies an axial pulling force in a direction (arrow 150) away from elongated insertion section 102. Because cover 124 is mechanically coupled to moveable member 107, moveable member 107 moves toward hub 105 against the bias applied by spring 116 which becomes compressed. At the same time, post 128 moves out of first axial section 146a and into circumferential section 146c of guide slot 146 of extension tube 103 and the spacing (S) between first clamping surface 122 and second clamping surface 118 becomes larger.

While maintaining the axial pulling force, the user rotates cover 124 in a clockwise direction (arrow 152) so that clamping surface 118 moves over engagement tabs 212 of medical instrument hub 210. In other words, opposing straight sides 127a which define opening 127 of cover 124 move over engagement tabs 212.

Figure 6C:
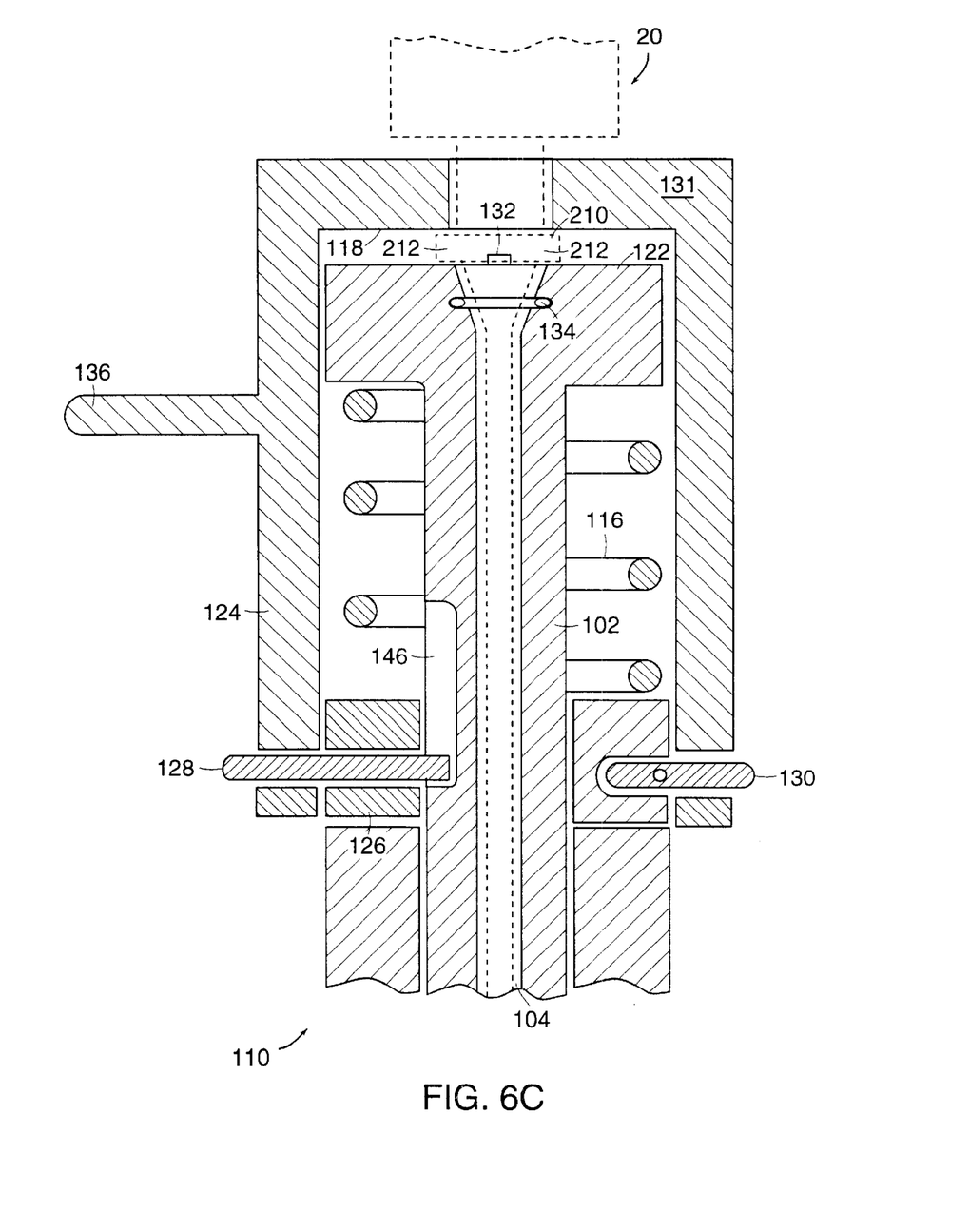
FIG. 6C is a cross-sectional view of the proximal end of the cannula in the closed position with a medical instrument shown in phantom and clamped firmly in place.

Referring to FIG. 6C, when the user releases the axial pulling force, clamping assembly 110 is moved into the closed position. Specifically, spring 116 forces moveable member 107 and cover 124 axially toward the elongated insertion section 102 so that engagement tabs 212 of medical instrument hub are clamped between first clamping surface 122 and second clamping surface 118. In this position, medical instrument 20 is firmly held within cannula 10 due to the constant clamping force applied by spring 116. Thus, medical instrument 20 is held tightly against seal 134, thereby ensuring that fluid does not leak from passage 104.

Because spacing S between first clamping surface 122 and second clamping surface 118 can be varied, the channel recess defined by the opposing clamping surfaces 118, 122 can accommodate a wide variety of medical instruments including those with differently sized and shaped Storz-type interfaces. Thus, a surgeon will more likely be able to interchange the use of medical instruments made by different manufacturers with cannula 10.

Figure 7:
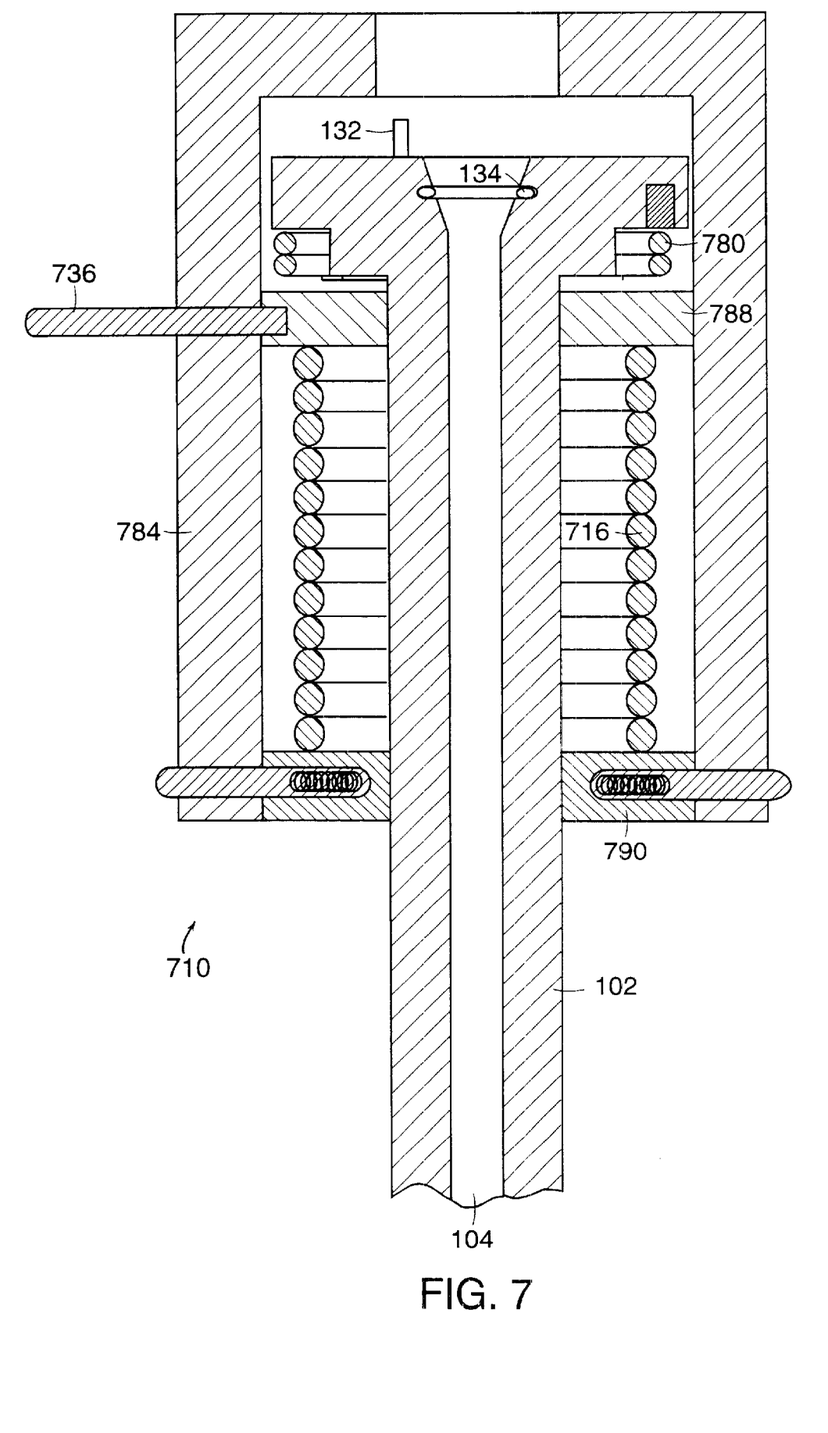
FIG. 7 is a cross-sectional view of the proximal end of an alternate embodiment of the cannula.

Referring now to FIG. 7, an alternative embodiment of a clamping assembly 710 is shown. Here, the clamping assembly 710 has the largely the same components as the previously described clamping assembly 110, however, a torsion spring 780 is used to control the rotational movement of a removable cover 784. In particular, torsion spring 780 is attached between removable cover 784 and a moveable member 788. The spring 788 is biased to hold clamping assembly 710 in its rotatably closed position.

To receive a medical instrument 20, the removable cover 784 must be both rotated to an open position, here using a finger post 736 against the bias of torsion spring 780, and pulled axially away from the elongated insertion section 102 against the bias of compression spring 716. Once a medical instrument 20 is received within the clamping assembly 720, the cover 720 is allowed to return to its rotatably and axially biased position, clamping the medical instrument between a surface of the cover and a surface of the elongated member as described above in connections with clamping assembly 110. Also, in this embodiment, an alternative removable finger post 736 has replaced the previous integral finger post 736 to allow cover 784 to be removed. Here, the removable finger post 736 is attached to the moveable member 788 which, in turn, is attached to spring 780.

Other embodiments are within the scope of the claims. For example, clamping assembly 110 of cannula 10, as described above, included an actuator in the form of moveable member 107 and cover 124, both of which, in operation, were moved and rotated to capture and engage the engaging portion of medical instrument 20. The invention however is intended as well to cover those embodiments in which, for example, the medical instrument is "actuated" in a manner that its engaging portion compresses the spring to widen the spacing between the clamping surfaces and then rotated to be clamped between the clamping surfaces. In addition, extension tube 103 was described above as a separate piece press-fit within elongated insertion member 102. In other embodiments, however, tube 103 can be formed integrally with elongated insertion member 102.

What is claimed is:

1. A cannula for receiving a medical instrument, the cannula comprising:
   an elongated insertion member having a proximal end with a first surface and a passage for receiving the medical instrument, the passage extending along an axis from the proximal end through a distal end of the insertion member;
   a clamping assembly disposed at the proximal end of the elongated insertion member to engage an engaging portion of the medical instrument, the clamping assembly having a second surface axially spaced from the first surface of the elongated insertion member and a biasing member positioned to bias at least one of the first surface and the second surface axially toward each other along said axis and configured to permit the second surface to move axially along and rotate about said axis of the elongated insertion member to engage the engaging portion of medical instrument between the first surface and the second surface; and
   a user-manipulatable actuator for manipulating the clamping assembly to move at least one of the first and second surfaces toward and away from each other, wherein the first surface and second surface are transverse to the axis of the elongated insertion member, the space between the first surface and second surface defining a channel for receiving the engaging portion of the medical instrument:
   wherein the actuator includes an opening sized to receive the engaging portion of the medical instrument;
   wherein the actuator is configured to be moved axially away from the elongated insertion section to allow the engaging portion of the medical instrument to be received within the channel and then rotated about an axis of the elongated insertion member to engage the engaging portion within the channel in a closed position; and
   wherein the opening is defined by a pair of opposing straight sides and a pair of opposing rounded sides, the opposing straight sides defining the second surface.

2. The cannula of claim 1 further comprising an alignment post extending from the first surface of the elongated insertion member to align the engaging portion of the medical instrument to the clamping assembly.

3. The cannula of claim 1 wherein the biasing member is a spring.

4. The cannula of claim 1 wherein the passage of the elongated insertion member includes an O-ring seal.

5. The cannula of claim 1 further comprising a torsion spring to bias the clamping assembly to remain in a rotatably closed position.

6. A cannula for receiving a medical instrument, the cannula comprising:
   an elongated insertion member having a proximal end with a first surface and a passage for receiving the medical instrument, the passage extending along an axis from the proximal end through a distal end of the insertion member;
   a clamping assembly disposed at the proximal end of the elongated insertion member to engage an engaging portion of the medical instrument, the clamping assembly having a second surface axially spaced from the first surface of the elongated insertion member and a biasing member positioned to bias at least one of the first surface and the second surface axially toward each other along said axis and configured to permit the second surface to move axially along and rotate about said axis of the elongated insertion member to engage the engaging portion of medical instrument between the first surface and the second surface; and
   a user-manipulatable actuator for manipulating the clamping assembly to move at least one of the first and second surfaces toward and away from each other,
   wherein the actuator includes a moveable member and the biasing member is positioned between the movable member and the elongated member.

7. The cannula of claim 6 wherein the first surface and second surface are transverse to the axis of the elongated insertion member, the space between the first surface and second surface defining a channel for receiving the engaging portion of the medical instrument.

8. The cannula of claim 7 wherein the actuator includes an opening sized to receive the engaging portion of the medical instrument.

9. The cannula of claim 8 wherein the actuator is configured to be moved axially away from the elongated insertion section to allow the engaging portion of the medical instrument to be received within the channel and then rotated about an axis of the elongated insertion member to engage the engaging portion within the channel in a closed position.

10. The cannula of claim 6 further comprising a cover and a post for mechanically coupling the moveable member to the cover.

11. The cannula of claim 10 wherein the elongated insertion member has a guide slot for receiving the post and guiding the clamping assembly between the opened and the closed positions.

12. The cannula of claim 11 wherein the guide slot includes a first section extending axially along the insertion section to a second section which extends circumferentially around the insertion section, the second section extending to a third section extending axially along the insertion section, the post positioned within the first and third sections in the open and closed positions respectively.

13. The cannula of claim 6 wherein the biasing member is positioned between the moveable member and the first surface, such that axial movement of the actuator toward the second surface compresses the biasing member.

14. A method of attaching a medical instrument to a cannula including an elongated insertion member having a proximal end with a first surface and a passage extending along an axis from the proximal end through a distal end of the insertion member, the method comprising:
   introducing the medical instrument through the passage: and using a clamping assembly to engage an engaging portion of the medical instrument to the proximal end of the elongated insertion member, the clamping assembly having a second surface axially spaced from the first surface of the elongated insertion member and a biasing member positioned to bias at least one of the first surface and the second surface axially toward each other along said axis and configured to permit the second surface to move axially along and rotate about said axis of the elongated insertion member to engage the engaging portion of medical instrument between the first surface and the second surface.

15. The method of claim 14 wherein using the clamping assembly further includes, manipulating a user-manipulatable actuator to move at least one of the first and second surfaces of the clamping assembly toward and away from each other.

16. The method of claim 15 wherein the first surface and second surface are transverse to the axis of the elongated insertion member and the space between the first surface and second surface define a channel for receiving the engaging portion of the medical instrument, the method further comprising:

moving the actuator axially away from the elongated insertion section to allow the engaging portion of the medical instrument to be received within the channel; and rotating the actuator about an axis of the elongated insertion member to engage the engaging portion within the channel in a closed position.

17. A clamping assembly for a cannula, the cannula including an elongated insertion member having a proximal end with a first surface and a passage for receiving the medical instrument, the passage extending along an axis from the proximal end through a distal end of the insertion member, the clamping assembly disposed at the proximal end of the elongated insertion member and comprising:

a member having a second surface axially spaced from the first surface of the elongated insertion member; and a biasing member positioned to bias at least one of the first surface and the second surface axially toward each other along said axis and configured to permit the second surface to move axially along and rotate about said axis of the elongated insertion member to engage the engaging portion of medical instrument between the first surface and the second surface, wherein the member is a user-manipulatable actuator for manipulating the clamping assembly to move at least one of the first and second surfaces toward and away from each other;

wherein the first surface and second surface are transverse to the axis of the elongated insertion member, the space between the first surface and second surface defining a channel for receiving the engaging portion of the medical instrument;

wherein the actuator includes an opening sized to receive the engaging portion of the medical instrument;

wherein the actuator is configured to be moved axially away from the elongated insertion section to allow the engaging portion of the medical instrument to be received within the channel and then rotated about an axis of the elongated insertion member to engage the engaging portion within the channel in a closed position; and wherein the opening is defined by a pair of opposing straight sides and a pair of opposing rounded sides, the opposing straight sides defining the second surface.

18. A clamping assembly for a cannula, the cannula including an elongated insertion member having a proximal end with a first surface and a passage for receiving the medical instrument, the passage extending along an axis from the proximal end through a distal end of the insertion member, the clamping assembly disposed at the proximal end of the elongated insertion member and comprising:

a member having a second surface axially spaced from the first surface of the elongated insertion member; and a biasing member positioned to bias at least one of the first surface and the second surface axially toward each other along said axis and configured to permit the second surface to move axially along and rotate about said axis of the elongated insertion member to engage the engaging portion of medical instrument between the first surface and the second surface, wherein the member is a user-manipulatable actuator for manipulating the clamping assembly to move at least one of the first and second surfaces toward and away from each other; and wherein the actuator includes a moveable member and the biasing member is positioned between the movable member and the elongated member.

19. The clamping assembly of claim 18 wherein the first surface and second surface are transverse to the axis of the elongated insertion member, the space between the first surface and second surface defining a channel for receiving the engaging portion of the medical instrument.

20. The clamping assembly of claim 19 wherein the actuator includes an opening sized to receive the engaging portion of the medical instrument.

21. The clamping assembly of claim 20 wherein the actuator is configured to be moved axially away from the elongated insertion section to allow the engaging portion of the medical instrument to be received within the channel and then rotated about an axis of the elongated insertion member to engage the engaging portion within the channel in a closed position.

\* \* \* \* \*